(12) United States Patent
Andrews

(10) Patent No.: US 6,213,132 B1
(45) Date of Patent: Apr. 10, 2001

(54) FLAT TOOTHPICK AND KIT

(76) Inventor: William M. Andrews, 424 Dundee, Barrington, IL (US) 60010

( * ) Notice: Subject to any disclaimer, the term of this patent is extended or adjusted under 35 U.S.C. 154(b) by 0 days.

(21) Appl. No.: 09/483,459

(22) Filed: Jan. 13, 2000

(51) Int. Cl.[7] .............................. A61C 15/00; A24F 27/00
(52) U.S. Cl. ......................... 132/321; 132/329; 206/104; 206/102
(58) Field of Search .................... 132/321, 329; 206/104, 581, 113, 63.5, 102

(56) References Cited

U.S. PATENT DOCUMENTS

| | | | |
|---|---|---|---|
| 1,451,380 | * | 4/1923 | Thum .................................. 132/329 |
| 2,111,265 | * | 3/1938 | Heckel ................................ 132/321 |
| 2,896,639 | * | 7/1959 | Fleming .............................. 132/321 |
| 3,438,486 | * | 4/1969 | Pinkas ................................. 132/321 |
| 3,910,293 | * | 10/1975 | Lemelson ............................ 132/321 |
| 3,913,596 | * | 10/1975 | Stuart ................................. 132/329 |
| 4,187,572 | * | 2/1980 | Savich .................................... 11/2 |
| 4,913,176 | * | 4/1990 | DeNiro ................................ 132/329 |
| 5,076,301 | * | 12/1991 | Sulskis ................................ 132/321 |
| 5,415,276 | * | 5/1995 | Welton ................................ 206/104 |
| 5,855,215 | * | 1/1999 | Clarke ................................. 132/321 |
| 6,044,848 | * | 4/2000 | Huang ................................. 132/321 |

* cited by examiner

Primary Examiner—John J. Wilson
Assistant Examiner—Robyn Kieu Doan
(74) Attorney, Agent, or Firm—Thomas R. Vigil

(57) ABSTRACT

The flat plastic toothpick comprises a thin sheet of plastic material having a somewhat tear-drop shape including a generally oval-shaped base section for gripping the toothpick and a generally curved or hook-shaped end section for being inserted into the interstice between two adjacent teeth. A kit is provided comprising two or more plastic sheets having a plurality of the toothpicks perforated therein.

16 Claims, 1 Drawing Sheet

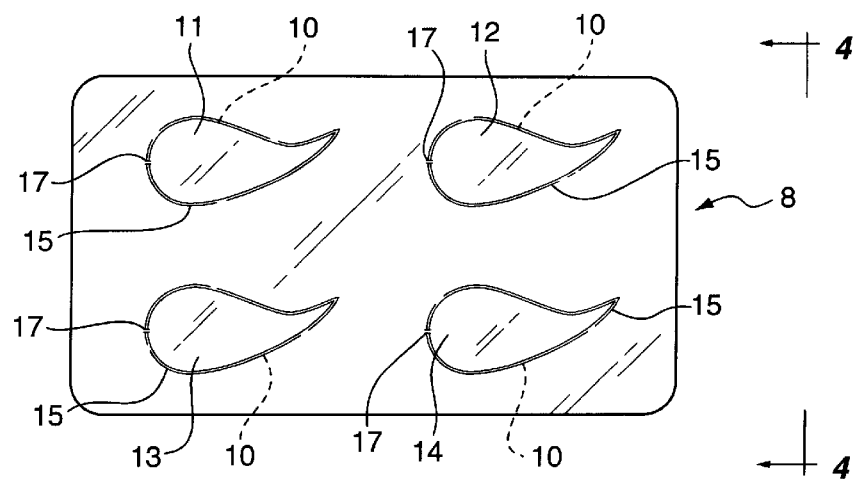
FIG. 1
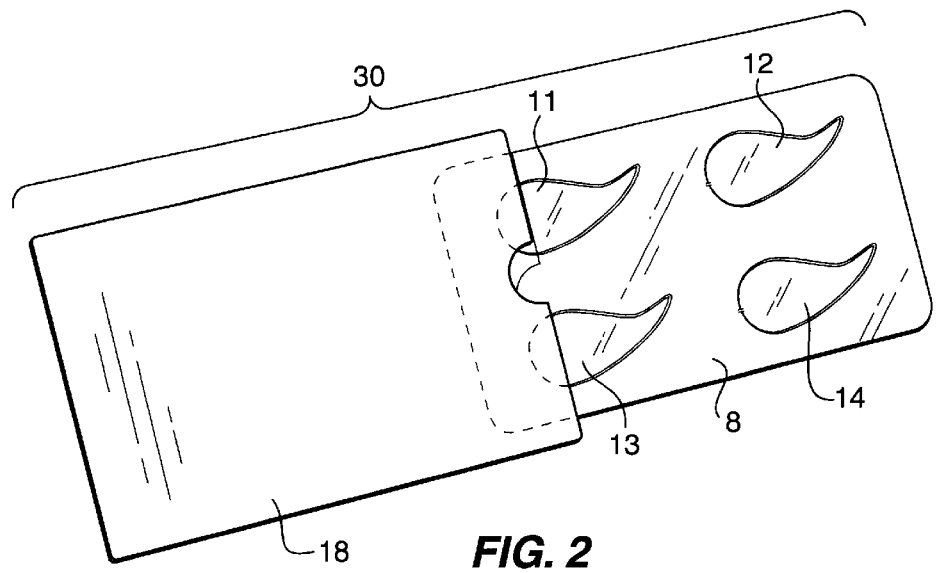
FIG. 2
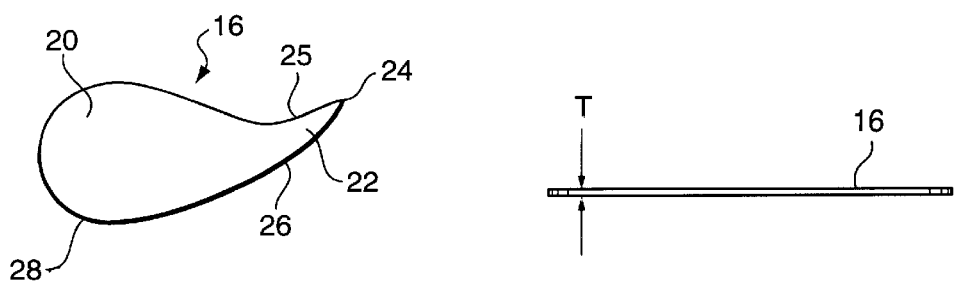
FIG. 3      FIG. 4

FLAT TOOTHPICK AND KIT

BACKGROUND OF THE INVENTION

1. Field of the Invention

The present invention relates to a flat plastic toothpick, and more specifically to a plastic sheet having a plurality, e.g. four, flat, somewhat tear-drop shaped, punch out or press out, toothpicks in a sheet of plastic combined with an envelope, preferably made of paper, for carrying the plastic sheet with the press out, somewhat tear-drop shaped toothpicks therein.

2. Description of the Prior Art

Heretofore flat end or flat shaped toothpicks have been proposed. Examples of such analogous and non-analogous toothpicks are disclosed in the following analogous and non-analogous U.S. Patents:

| U.S. Pat. No. | Patentee |
| --- | --- |
| 3,978,872 | Bond |
| 4,312,370 | Hinge |
| 5,119,941 | Lepie |
| 5,234,009 | Lemon et al. |
| 5,415,276 | Welton |
| 5,560,379 | Pieczenik |
| 5,693,360 | Stern et al. |
| 5,823,208 | Lin |
| 5,868,149 | Yang |

The Bond U.S. Pat. No. 3,978,872 discloses a generally rectangular or square-in-cross-section toothpick having ends which are tapered to a thin bladed end of each end of the toothpick.

The Hinge U.S. Pat. No. 4,312,370 discloses a toothpick comprising an elongated section of thin corrugated plastic material which is curved so that one end defines a projecting point. The plastic material is quite thin to enable the parts of the toothpick to move between adjacent teeth.

The Lepie U.S. Pat. No. 5,119,941 discloses a matchbook-shaped structure which includes a plurality of individually packaged dental floss members detachably secured to the matchbook-like structure. Each dental floss member comprises a plurality of rows of individual packages or strands that have gripping ends at each end of the strand and they are joined to adjacent gripping ends via perforations. The plurality of gripping end members are secured to the matchbook-like structure.

The Lemon et al. U.S. Pat. No. 5,234,009 discloses a toothpick which has pointed knife-like tips at opposite ends that curve upwardly and which has sides that taper inwardly to each knife-like tip.

The Welton U.S. Pat. No. 5,415,276 discloses a portable toothpick packet with flat toothpicks in a rectangular perforated wood or plastic sheet. The toothpicks are triangular in shape and the perforations are two diagonal lines in the rectangular sheet.

The Pieczenik U.S. Pat. No. 5,560,379 discloses a dental paper pick and flosser defined by a rectangular sheet of siliconized paper having one diagonal line of perforations to define two flat picks in each sheet of a stack of sheets.

The Stern et al. U.S. Pat. No. 5,693,360 discloses a toothpick and method for the manufacture thereof. The toothpick includes a blade of elastic plastic material which extends outwardly from a thicker, oval shaped base to a thin cleaning tip that curves upwardly.

SUMMARY OF THE INVENTION

According to the present invention there is provided a flat toothpick comprising a thin sheet of plastic material having a somewhat tear-drop shape including a generally oval-shaped base section for gripping the toothpick and a generally curved or hook-shaped end section for being inserted into the interstice between two adjacent teeth and a kit of plastic sheets having a plurality of the toothpicks perforated therein.

BRIEF DESCRIPTION OF THE DRAWINGS

FIG. 1 is a top plan view of a sheet of plastic material constructed according to the teachings of the present invention having perforations therein which form four, somewhat tear-drop shaped toothpicks.

FIG. 2 is a perspective view of the sheet shown in FIG. 1, together with a paper or plastic envelope for receiving same.

FIG. 3 is a plan view of one, somewhat tear-drop shaped toothpick which has been pressed from the sheet shown in FIG. 1.

FIG. 4 is an end view of the sheet of material shown in FIG. 1 and is taken along line 4—4 of FIG. 1.

DESCRIPTION OF THE PREFERRED EMBODIMENT(S)

Referring now to the drawings in greater detail, there is illustrated in FIG. 1 a sheet 8 of plastic material having a plurality, namely four, of continuous cutouts 10, each defining a somewhat tear-drop shaped toothpick structure 11, 12, 13 and 14, each of which can be pressed out of the sheet 8 to form a generally, tear-drop shaped, thin flat plastic toothpick 16. Each toothpick structure 11–14 is defined by a cut line 15 which extends completely around each toothpick structure 11–14, except for a small bridge 17 of material at the bottom of each toothpick structure 11–14, whereby one of the toothpick structures 11–14 can be torn away easily from the sheet 8 by tearing through the bridge 17.

One flat somewhat tear-drop shaped toothpick 16 is shown in FIG. 3.

Referring now to FIG. 2, there is illustrated therein the sheet 8 shown in FIG. 1 extending partially out of an envelope 18 which can be made of plastic or paper and is preferably made of a spunbonded olefin material sold under the trademark TYVEK.

As best shown in FIG. 3, each toothpick 16 has a generally oblong or oval-shaped base section 20 and a generally hook-shaped end section 22 that curves or hooks upwardly on one side of the generally oval-shaped base section 20 of the toothpick 16 to a point 24. From the point 24, a top edge 25 of the toothpick 16 extends rearwardly and steeply upwardly to the generally oval-shaped base section 20, as shown in FIG. 3. Also, from the generally oval-shaped base section 20, a bottom edge 26 curves slightly downwardly and merges with a peripheral edge 28 of the generally, oval-shaped base section 20.

The oblong or oval-shaped base section 20 has a sufficient area to enable the toothpick 16 to be gripped by and between the thumb and forefinger of a user so that the tip section 22 can then be inserted into an interstice between two adjacent teeth for removing material stuck or caught between the two teeth. Typically, the generally oval-shaped base section 20 has a length toward the end section 22 of from 0.20 inch to 1.00 inch, and preferably 0.30 inch to 0.40 inch. Then, the generally oval-shaped base section has a width of from 0.20 inch to 0.80 inch, and preferably is between 0.30 inch and 0.40 inch.

The length of the end section 22 is between 0.20 inch and 0.80 inch, and preferably between 0.30 and 0.60 inch. The angle subtending the tip is between 20 degrees and 60 degrees, and preferably around 30 degrees.

To enable the flat toothpick to extend between two teeth, the thickness or width T of the toothpick is between 2 mil and 10 mil, and preferably about 5 mil.

According to the present invention, a plurality of sheets 8 are provided such that one to ten sheets 8 can be carried in the envelope 18 to form a toothpick kit 30 comprising one to ten sheets 8, together with the envelope 18 shown in FIG. 2. The sheet or sheets 8 are carried in the envelope 18, both of which have a shape generally the same as the shape of a credit card, e.g., 1.9 inch to 2.4 inch by 3.0 inch to 3.5 inch.

Also, it will be appreciated that an individual toothpick 16 punched from one of the sheets 8 can be carried by itself or with other toothpicks 16 in the envelope 18.

The plastic material from which the sheet 8 is made can be any standard appropriate plastic material, such as polyethylene, polypropylene, polyvinyl chloride, etc.

From the foregoing description, it will be appreciated that the toothpick kit 30 and the flat toothpicks 16 which can be punched out from the sheet 8 of material in the kit 30 have a number of advantages, some of which have been described above and others of which are inherent in the kit 30, sheet 8 and toothpick 16 of the present invention. Moreover, it will be understood that modifications can be made to the kit 30, sheet 8 and toothpick 16 without departing from the teachings of the invention. Accordingly, the scope of the invention is only to be limited as necessitated by the accompanying claims.

I claim:

1. A toothpick kit comprising a sheet of plastic material having a thickness between 2 mil and 10 mil and having a plurality of approximately tear-drop shaped flat plastic toothpicks cut therein except for a small bridge of material, each plastic toothpick being adapted to be punched or torn out from said sheet of thin plastic material and each flat plastic toothpick with said approximately tear-drop shape having the same thickness throughout and including a generally oval-shaped base section for gripping the toothpick and a generally curved or hook-shaped end section for being inserted into the interstice between two adjacent teeth.

2. The plastic toothpick of claim 1 being made of a plastic material selected from the group consisting of polyurethyene, polyethylene, and polyvinyl chloride.

3. The plastic toothpick of claim 1 wherein said thickness of said plastic sheet is approximately 5 mil.

4. The plastic toothpick of claim 1 wherein said generally oval-shaped base section has a length between approximately 0.2 inch and approximately 1.0 inch.

5. The plastic toothpick of claim 1 wherein said generally oval-shaped base section has a width between approximately 0.2 inch and approximately 0.8 inch.

6. The plastic toothpick of claim 1 wherein said generally oval-shaped base section has a length between approximately 0.3 and 0.4 inch and a width between approximately 0.3 inch and 0.4 inch.

7. The plastic toothpick of claim 1 wherein said generally hook-shaped end section has a length of approximately 0.2 inch and approximately 0.8 inch.

8. The plastic toothpick of claim 1 wherein said generally hook-shaped end section has a width of approximately 0.2 inch adjacent said generally oval shaped end section.

9. The toothpick kit of claim 1 wherein said plastic sheet has four continuous cut lines except for four bridges of material therein for punching or tearing out four toothpicks from said sheet.

10. The toothpick kit of claim 1 including an envelope which is sized to receive said sheet of plastic material.

11. The toothpick kit of claim 10 wherein said envelope is constructed to receive a plurality of said sheets of plastic material.

12. The toothpick kit of claim 10 wherein said envelope is constructed to receive up to ten sheets of plastic material.

13. The toothpick kit of claim 10 wherein said envelope is made of a plastic material.

14. The toothpick kit of claim 10 wherein said envelope is made of a spunbonded olefin material.

15. The toothpick kit of claim 10 wherein said envelope comprises two sheets of paper sealed along three edges, leaving one edge open for receipt of one or more sheets of plastic having flat toothpicks.

16. The toothpick kit of claim 1 wherein said plastic sheet has a width between approximately 1.9 inch and approximately 2.4 inch and a length between approximately 3.0 inch and approximately 3.5 inch.

* * * * *